US008758838B2

(12) United States Patent
Holland et al.

(10) Patent No.: US 8,758,838 B2
(45) Date of Patent: Jun. 24, 2014

(54) ANTI-INFLAMMATORY COMPOSITIONS AND METHODS OF USE

(75) Inventors: Jean Holland, Doylestown, PA (US); Janeta Nikolovski, Princeton, NJ (US); Peter Lyte, Princeton, NJ (US); Michael Southall, Lawrenceville, NJ (US); Vivian Zhu, Flemington, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 11/215,912

(22) Filed: Aug. 31, 2005

(65) Prior Publication Data

US 2007/0048396 A1 Mar. 1, 2007

(51) Int. Cl.
*A61K 36/28* (2006.01)
*A61K 36/63* (2006.01)

(52) U.S. Cl.
CPC ..................................... *A61K 36/63* (2013.01)
USPC ........................................................ 424/764

(58) Field of Classification Search
None
See application file for complete search history.

(56) References Cited

U.S. PATENT DOCUMENTS

| 6,346,239 | B1 | 2/2002 | Mallo et al. |
| 6,440,432 | B1 | 8/2002 | Mukherjee et al. |
| 6,488,946 | B1 * | 12/2002 | Milius et al. ................... 424/401 |
| 6,762,158 | B2 | 7/2004 | Lukenbach et al. |
| 7,871,635 | B2 | 1/2011 | Stolz et al. |
| 8,089,478 | B2 | 1/2012 | Hariya et al. |
| 2001/0002257 | A1 | 5/2001 | Stolz |
| 2002/0164386 | A1 * | 11/2002 | Meisner ...................... 424/725.1 |
| 2003/0170331 | A1 | 9/2003 | Cals-Grierson et al. |
| 2003/0224028 | A1 | 12/2003 | Galey |
| 2004/0166079 | A1 | 8/2004 | Garcia |
| 2005/0003023 | A1 | 1/2005 | Meisner |
| 2005/0129759 | A1 * | 6/2005 | Sojka ............................ 424/469 |
| 2005/0186269 | A1 | 8/2005 | Udell et al. |
| 2007/0048396 | A1 | 3/2007 | Holland et al. |
| 2007/0048397 | A1 | 3/2007 | Holland et al. |

FOREIGN PATENT DOCUMENTS

| EP | 0273202 B1 | 6/1995 |
| EP | 273202 B1 | 6/1995 |
| EP | 0937455 B1 | 1/2004 |
| EP | 1 561 457 A2 | 8/2005 |
| EP | 1561457 B1 | 8/2005 |
| FR | 2507477 | 12/1982 |
| FR | 2 848 116 A1 | 6/2001 |
| JP | 58023612 A | 2/1983 |
| JP | 2006-6172152 A | 6/1994 |
| JP | 09157172 A | 6/1997 |
| JP | 2000063224 A | 2/2000 |
| JP | 2000-247829 A | 9/2000 |
| JP | 2001-002550 | 1/2001 |
| JP | 2001002550 A * | 1/2001 |
| JP | 2002-012548 A | 1/2002 |
| JP | 2002-332238 A | 11/2002 |
| JP | 2002332238 A * | 11/2002 |
| JP | 2008-040921 | 8/2006 |
| SE | 453724 B | 2/1988 |
| WO | 9805338 A | 2/1998 |
| WO | 9840074 A | 9/1998 |
| WO | 0182940 A1 | 11/2001 |
| WO | WO 0182940 A1 * | 11/2001 |
| WO | 0247644 A1 | 6/2002 |
| WO | 2004/022028 A1 | 3/2004 |
| WO | 2005/063195 A2 | 7/2005 |

OTHER PUBLICATIONS http://web.archive.org/web/*/http://skincarerx.com/lipikaring.html (Web Publication Date:Jul. 25, 2003 ). Date Accessed: Dec. 24, 2006.*
http://web.archive.org/web/*/http://www.ahavaus.com/ (Web Publication Date: Feb. 7, 2005). Date Accessed: Dec. 24, 2006.*
"Heat Rash". Internet Archive Date: Sep. 21, 2004 [Retrieved on: Nov. 18, 2007]. Retrieved from the Internet: <http://web.archive.org/web/*/http://www.medicinenet.com/heat_rash/article.htm>.*
"Olive Leaf". Internet Archive Date: Apr. 19, 2002 [Retrieved on: Nov. 18, 2007]. Retrieved from the Internet: <http://web.archive.org/web/*/http://www.raysahelian.com/oliveleaf.html>.*
"Skincare for Severely Dry Skin". Internet Archive Date: Jul. 25, 2003. [Retrieved on: Dec. 24, 2006]. Retrieved from the Internet: <http://web.archive.org/web/*/http://skincarerx.com/lipikaring.html>.*
"Ahava: Essential Dead Sea Treatment". Internet Archive Date: Feb. 7, 2005 [Retrieved on: Dec. 24, 2006] Retrieved from the Internet: <http://web.archive.org/web/*/http://skincarerx.com/lipikaring.html>.*
(U1) Dinop. Internet Archive Date: Dec. 31, 2004 [Retrieved from the Internet on: Aug. 28, 2008]. Retrieved from: <http://www.adinop.co.th/product_cosmetics_show.php?subgroup_id=201>.*
(V1) "Get the Red out". Internet Archive Date: May 12, 2003 [Retrieved from the Internet on: Aug. 27, 2008]. Retrieved from: <http://www.healthyskinshop.com/stresoutskin.html>.*
International search report PCT/FR02/03510 dated Jan. 22, 2003.
Gonzalez et al., "Hypoglycemic Activity of Olive Leaf"; Planta Medica Journal of Medicinal Plant Research, vol. 58, Feb. 1992, pp. 513-515.
Seppic, "Sepicalms", A Soothing Active Ingredient Specially Adapted to the Needs of Sensitive Skin; Oct. 2001, pp. 1-42.
Fehri et al., "Olea Europaea L: Stimulant, Anti-ulcer and Anti-inflammatory Effects"; Boll. Chim. Farmaceutico, Jan. 1, 1996.
Disclosed Anonymously, "Sepicalm S: Sodium cocoyl aminoacids & sarcosine & potassium aspartate & magnesium aspartate: Effet apaisant, relaxant, antioxydant, antiradicalaire, antiage, remodelant, hydratant antipelliculaire, seboregulateur, normalisateur des peaux a tendance acneique, purifiant, eclaircissant, raffermissant, amincissant", IP.com Journal, May 28, 2004.

(Continued)

*Primary Examiner* — Amy L Clark

(57) ABSTRACT

Provided are anti-inflammatory compositions comprising (a) an anti-inflammatory agent selected from the group consisting of olive leaf extract, holly herb, sappan wood, feverfew, and combinations of two or more thereof, and (b) an anti-inflammatory agent comprising at least one lipophilic aminoacid and at least one metal salt. Also provided are personal care products comprising such compositions, and methods of use thereof.

5 Claims, No Drawings

(56) References Cited

OTHER PUBLICATIONS

Chou et al., "Quantitative Analysis of Dose-Effect Relationships: The combined Effects of Multiple Drugs or Enzyme Inhibitors", Advances in Enzyme Regulations, Pergamon Press, Oxford, GB, vol. 22, Jan. 1, 1984, pp. 27-55, XP023796270, ISSN: 0065-2571, DOI: 10.1016/0065-2571(84)90007-4 [retrieved on Jan. 1, 1984].

Anonymous, "Sepicalm S Sodium Cocoyl Aminoacids Sarcosine Potassium Aspartate Magnesium Aspartate: Effet Apaisant, Relaxant, Antioxydant, Antiradicalaire, Antiage, Remodelant,hydratant Antipelliculaire, Seboregulateur, Normalisateur Des Peaux A tendance Acneiue, Purifiant, Eclaiarcissant, Reffermissant, Amin", May 28, 2004, IP.COM Inc., XP013020410.

Anonymous, "New Formulations for, e.g., Firming Oil and Spray, Restructuring Dressing Gel, Deodorant Cream and Spray, Anti-Aging Revitalizing Cream, or Facial Cleanser", Accession No. 2001-406371, 2001 XP0026585623.

Anonymous, "Water Lily-Nymphaea Alba", Herbs for Life, Mar. 11, 2011, XP002685616.

Anonymous, "Nenupar Blanc", Plantes Sauvages, Oct. 18, 2012, XP002685617.

Anonymous, "Sepicalm VG Whitens, Lightens and Soothes The Skin", Aug. 1, 2007, XP002685618.

Anonymous, "Soin Hydratant Destressant", Jan. 1999, XP002685619.

Anonymous, "Bath & Shower Product", Jun. 2003, Accession No. 210393, XP002685620.

Anonymous, "White Lotus Creamy-White Day Cream Sparking Face", Feb. 4, 2000, XP002685621.

Braun, L., 'Olive-Leaf Extract Olea Europaea, Journal of Complementary Medicine, vol. 4, No. 3, May 1, 2005, XP055041690.

Choi, E., et al., "Investigations of Anti-Inflammatory and Anticociceptive Activities of Piper Cubeba, Physalis Angulata and Rosa Hybride", Journal of Ethnopharmacology, vol. 89, No. 1, Nov. 1, 2003, XP009092358.

De Nino, A., et al. "Absolute Method for the Assay of Oleuropein in Olive Oils by Atmospheric Pressure Chemical Ionization Tandem Mass Spectrometry", Anal. Chem., vol. 77, pp. 5961-5964 (2005).

Mukherjee, P., et al. The Sacred Lotus Journal of Pharmacy and Pharmacology, vol. 61, No. 4, Apr. 1, 2009, XP055041589.

Ormerod, et al., "An Investigation into the Effect of the Nitric Oxide Synthase Antagonist L-NAME and Plant Extracts on the Irritability and Barrier Function of the Skin", Exogenous Dermatology: Physical-Chemical-Biological, vol. 2, No. 6, pp. 295-300, Jan. 1, 2003, XP009163937.

Perri, E., et al. "quantitation of Oleuropein in Virgin Olive Oil by Ionspray Mass Spectrometry-Selected reacton Monitoring", J. Agric. Food Chem., vol. 47, pp. 4156-4160 (1999).

Savournin, C., et al. "Rapid High-Performance Liquid Chromatolgraphy Analyss for the Quantitative Determination of Oleuropein in *Olea europaea Leaves*", J. Agric. Food Chem. vol. 49, pp. 618-621 (2001).

Vigo, E., et al. In-Vitro Anti-Inflammatory Effect of 1 Eucalyptus Globulus and Thymus Vulgaris : Nitric Oxide Inhibition in J774A.1 Murine Macrophages, Journal of Pharmacy and Pharmacology, vol. 56, No. 2, pp. 257-263, Feb. 1, 2004, XP055041590.

"Use of a facial moisturizer containing palmitoyl pentapeptide improves the appearance of aging skin", J. of the American Academy of Dermatology, vol. 52, No. 3, Mar. 1, 2005, p. P96, XP004840578 ISSN: 0190-9622.

http://web.archive.org/web/*/http://skincarerx.com/lipikaring.html (web publication date: Jul. 25, 2003).

http://web.archive.org/web/*/http://www.ahavaus.com/ (web publication date: Feb. 7, 2005.

"Heat Rash". Internet Archive Date Sep. 21, 2004 http://web.archive.org/web/*/http://www.medicinenet.com/heat_rash/article.htm.

"Olive Leaf". Internet Archive Date: Apr. 19, 2002 http://web.archive.org/web/*/http://www.raysahelian.com/oliveleaf.htm.

"Skincare for Severely Dry Skin". Internet Archive Date: Jul. 25, 2003 http://web.archive.org/web/*/http://skincarerx.com/lipikaring.html.

"Ahava: Essential Dead Sea Treatment". Internet Archive Date: Feb. 7, 2003 http://web.archive.org/web/*/http://skincarerx.com/lipikaring.html.

Dinop. Internet Archive Date: Dec. 31, 2004 http://www.adinop.co.th/product_cosmetics_show.php?subgroup_id=201.

"Get the Red Out". Internet Archive Date: May 12, 2003 http://www.healthyskinshop.com/stresoutskin.html.

"NutriTeam" Olive Leaf. Internet Archive Date: 2000-07-2011 http://web.archive.org/web/20000711062558/http:nutriteam.com/oliveleaf.htm.

Suzman. Food and Wine. "Beauty of Olive Oil" Published Jun. 2001 http://www.foodandwine.com/articles/olive-oil.

Australian Examination report for corresponding Application No. 2005335943 dated Apr. 20, 2011.

European Search Report for corresponding Application No. 05801043.0-2107 dated Oct. 23, 2012.

Japanese Reasons for Rejection for corresponding Application No. 2008-528998 dated Oct. 9, 2012.

Japanese Reasons for Rejection for corresponding Application No. 2008-528998 dated Oct. 11, 2011.

PCT International Search Report for corresponding Application No. PCT/US05/34398 dated May 12, 2006.

* cited by examiner

ANTI-INFLAMMATORY COMPOSITIONS AND METHODS OF USE

FIELD OF THE INVENTION

The present invention relates to compositions that tend to exhibit anti-inflammatory properties, and more particularly, to compositions comprising combinations of anti-inflammatory agents, which compositions tend to exhibit unexpectedly high, synergistic anti-inflammatory properties as compared to conventional compositions.

BACKGROUND

A wide variety of skin care actives suitable for use in personal care compositions are known. Examples of such skin care actives include olive leaf extract, which has been described as exhibiting antihypertensive and hypoglycemic activities, antiradical properties for alimentary and cosmetics, and anti-inflammatory activity when given via the oral route (see, for example, Leaf extract of *Olea europea* rich in oleuropeine, products from it, their application as medicines and compositions containing them. Combes, Georges; Escaut, Alexandre. Fr. Demande, FR 2507477 A1 19821217, 1982; Gonzalez M, et al, *Hypoglycemic activity of olive leaf, Planta Med* December 1992; 58(6):513-515; Use of an extract from the leaves of *Olea Europea* as an antiradical agent. Amari, Giorgio. Eur. Pat. Appl. (1999), EP 937455 A1 19990825; Fehri B, et al. *Olea europaea L.: stimulant, anti-ulcer and antiinflammatory effects. Boll Chim Farm* (1996) 135(1): 42-49), Sigesbeckia (Holy Herb), which has been used as a remedy for ague, rheumatism, renal colic, and as a cure for ringworm in conjunction with glycerine, *Lignum Sappan* (Sappan Wood), which has been used to promote blood circulation and remove blood stasis, and to cause subsidence of swelling and relieve pain, and Feverfew, recognized as having significant medicinal properties when taken orally and used as a general febrifuge. Other skin care actives include oil extracts a such as *Boswellia Serrata* oil extract (Frankincense), described as exhibiting anti-tumor and anti-arthritic properties, and oat oil extract, described as exhibiting anti-irritant and an antioxidant properties.

Applicants have recognized the need to develop combinations of skin care actives to effectively treat, reduce, and/or prevent inflammation of the skin due to any of a variety of sources. While applicants have recognized a variety of actives that tend to exhibit anti-inflammatory properties, it is generally difficult, if not impossible, to predict combinations of such actives that will exhibit unexpectedly high, synergistic anti-inflammatory properties and effectiveness at reducing inflammation.

In addition, applicants have recognized that in certain uses it may be desirable to use relatively low amounts of actives from a cost perspective, to reduce undesirable color or odor associated with certain actives, for stability reasons, and the like. However, many actives, or combinations thereof, tend to exhibit relatively little or no effectiveness at reducing inflammation when applied in relatively low amounts. Accordingly, applicants have identified the need for combinations of skin care actives that exhibit relatively high, synergistic anti-inflammatory properties and effectiveness, and certain combinations that may further be effective even in relatively low amounts.

SUMMARY OF INVENTION

Applicants have discovered compositions that meet the outstanding need for combinations of skin care actives that exhibit unexpectedly high, synergistic anti-inflammatory properties. In addition, applicants have recognized that certain of such compositions exhibit surprisingly high anti-inflammatory properties in relatively low amounts.

According to certain embodiments, the present invention provides compositions comprising (a) an anti-inflammatory agent selected from the group consisting of olive leaf extracts, holly herb, sappan wood, feverfew, and combinations of two or more thereof, and (b) an anti-inflammatory agent comprising at least one lipoaminoacid and at least one metal salt.

According to certain other embodiments, the present invention provides personal care products comprising a composition of the present invention.

In yet further embodiments, the present invention provides methods of treating/reducing inflammation and/or redness by contacting skin in need of inflammation reduction with a composition of the present invention and/or contacting skin in need of inflammation reduction with a personal care product of the present invention.

DESCRIPTION OF PREFERRED EMBODIMENTS

According to certain preferred embodiments, the present invention provides compositions comprising (a) an anti-inflammatory agent comprising olive leaf extract, holly herb, sappan wood, feverfew, or combinations of two or more thereof, and (b) an anti-inflammatory agent comprising at least one lipoaminoacid or salt thereof and at least one metal salt. Applicants have discovered unexpectedly that such combinations of anti-inflammatory agents exhibit synergistic and unexpectedly high anti-inflammatory properties, in particular, the compositions of the claimed invention exhibit anti-inflammatory properties that are greater than, and often about 1.2 times to greater than about 1.8 times greater than, the sum of the anti-inflammatory properties of the individual active components.

As used herein, the term "anti-inflammatory agent" refers generally to any compound or combination of compounds that, upon introduction to skin which exhibits inflammation, tends to reduce such inflammation. Examples of actives suitable for use in the present invention include olive leaf extracts, including any water or oil-soluble extracts of *Olea europea*, as well as, holly herb, sappan wood, feverfew, combinations of two or more thereof, and the like. In certain preferred embodiments, the active comprises olive leaf extract. Many of such suitable actives are commercially available from one or more sources, for example, olive leaf extract (water-soluble extract available from B&T srl (Milano, Italy) under the trade name Eurol BT and oil-soluble extract available from Active Organics), holy herb (available from Sederma Edison N.J.), and feverfew (available from Indena, Milan Italy), and the like.

Any suitable, cosmetically-acceptable anti-inflammatory agent comprising at least one lipoamino acid and at least one metal salt may be used herein. Examples of suitable lipoamino acids include those produced by linking amino acids, such as alanine, glycine, glutamic acid, aspartic acid, and the like, to fatty acid chains, such as, for example, cocoyl or other chains, and salts derived therefrom. Certain preferred lipoamino acids include cocoyl aminoacids (formed by linking alanine, glycine, glutamic acid, and aspartic acid to cocoyl moieties), and salts thereof, including sodium salts, potassium salts, and the like. Certain particularly preferred lipoamino acids comprise sodium cocoyl aminoacids. Examples of suitable metal salts include sodium, potassium, calcium, magnesium salts, combinations of two or more and the like. Certain preferred metal salts include aspartates, gluconates, glycophosphates, and the like. Certain preferred anti-inflammatory agents comprise at least one lipoamino acid and at least one metal aspartate. Certain more preferred agents comprises one or more lipoamino acids and at least two metal aspartates. For example, a particularly preferred anti-inflammatory agent comprises a combination of sodium cocoyl aminoacids, magnesium aspartate, and potassium aspartate (in combination with sarcosine) available commercially from Seppic under the trade names Sepicalm S and Sepicalm S WP.

Any suitable amounts of (a) anti-inflammatory agent selected from the group consisting of olive leaf extract, holly herb, sappan wood, feverfew, and combinations of two or more thereof ("agent (a)") and (b) anti-inflammatory agent comprising at least one lipoamino acid and at least one metal salt ("agent(b)") may be used in the present invention. In certain embodiments, the present compositions comprise from greater than zero to less than 100 weight percent of agent (a) and from less than 100 to greater than zero weight percent of agent (b) (as used herein and throughout, the term "weight percent" means the percent by weight, on an active basis, of an agent based on the total active weight of agent (a) and agent (b) unless specifically described otherwise). In certain preferred embodiments, the compositions comprise from about 10 to about 90 weight percent of agent (a) and from about 90 to about 10 weight percent of agent (b), more preferably from about 20 to about 80 weight percent of agent (a) and from about 80 to about 20 weight percent of agent (b), and even more preferably from about 40 to about 60 weight percent of agent (a) and from about 60 to about 40 weight percent of agent (b).

In certain preferred embodiments, the weight ratio of agent (a) to agent (b) is from about 4:1 to about 1:4. In certain other preferred embodiments, the ratio is from about 2:1 to about 1:2, and in other embodiments preferably about 1:1.

The compositions of the present invention may further include any of a variety of additional anti-inflammatory and other cosmetically-active agents in addition to agent (a) and agent (b). A "cosmetically active agent" is a compound that has a cosmetic or therapeutic effect on the skin, e.g., agents to treat wrinkles, acne, or to lighten the skin. In one embodiment, the agent is selected from, but not limited to, the group consisting of: hydroxy acids; benzoyl peroxide; sulfur resorcinol; D-panthenol; hydroquinone; anti-inflammatory agents; skin lightening agents; antimicrobial and antifungal agents such a miconazole, ketoconazole, and elubial; vitamins such as ascorbic acid; tocopherols and tocotrienols such as tocopheryl acetate; retinoids such retinol, retinal, retinyl palmitate, retinyl acetate, and retinoic acid; hormones such as estrogens and dihydroxyandrostene dione; 2-dimethylaminoethanol; lipoic acid; amino acids such a proline and tyrosine; lactobionic acid; self-tanning agents such as dihydroxy acetone; dimethyl aminoethanol; acetyl-coenzyme A; niacin; riboflavin; thiamin; ribose; electron transporters such as NADH and FADH2; botanical extracts such as ginkgo biloba, aloe vera, and soy; and derivatives thereof. Examples of hydroxy acids include, but are not limited, to (i) alpha-hydroxy acids such as glycolic acid, lactic acid, malic acid, citric acid, and tartaric acid, (ii) beta-hydroxy acids such as salicylic acid, and/or (iii) polyhydroxy acids. See, e.g., European Patent Application No. 273,202. Examples of derivatives of ascorbic acid include, but are not limited to, ascorbyl palmitate, magnesium ascorbyl phosphate, sodium ascorbyl phosphate, zinc ascorbyl phosphate, ascorbyl glucoside, sodium ascorbate, and ascorbyl polypeptide. An example of a derivative of hydroquinone includes, but is not limited to, arbutin. In certain preferred embodiments, the composition of the present invention further comprises one or more tocopherols and/or tocopherol esters such as tocopherol acetate.

Applicants have recognized that the compositions of the instant invention, exhibiting unexpectedly high anti-inflammatory properties, may be used to great advantage in any of a number of personal/health care products. For example, the present compositions may be used in creams, lotions, balms, washes, gels, sticks, sprays, ointments, mousses, and cosmetics/make-up. These products may comprise several types of cosmetically-acceptable carrier systems including, but not limited to single phase solutions (e.g., oil based solutions), emulsions, and gels. The term "cosmetically-acceptable topical carrier" refers to a carrier for topical use that is capable of having the other ingredients dispersed or dissolved therein, and possessing acceptable safety properties. The personal care products may be intended for use in skin care, infant care, women's health, wound care, combinations of two or more thereof, and the like, by consumers. Such products may be marketed for any of a variety of benefits including diaper rash reduction, anti-acne, anti-aging, UV protection, soothing, moisturizing, combinations of two or more thereof, and the like.

The personal/health care products comprising the agent composition of the present invention may further include any of a variety of materials used conventionally in personal care products. For example, one or more anionic, nonionic, amphoteric, and/or cationic surfactants, pearlescent or opacifying agents, thickening agents, secondary conditioners, humectants, chelating agents, and additives which enhance the appearance, feel and fragrance of the compositions, such as colorants, fragrances, preservatives, pH adjusting agents, and the like may be used.

The personal care products produced according to the present invention may comprise any suitable amounts of the present anti-inflammatory compositions. Applicants have recognized surprisingly that the compositions of the present invention have a significant anti-inflammatory benefits even when present in personal care formulations in relatively low amounts, for example as low as about 0.02 active weight percent, or less, based on the total weight of the personal care product (herein after the "composition weight percent in product"). Accordingly, the personal care products of the present invention may comprise from greater than zero to about 5 composition weight percent in product, including from about 0.02 to about 4 composition weight percent in product, from about 0.1 to about 2 composition weight percent in product, and from about 0.1 to about 1 composition weight percent in product. In certain preferred embodiments, the personal care products comprise from greater than zero to about 1 composition weight percent in product, more preferably from about 0.02 to about 0.5 weight percent in product, and even more preferably from about 0.02 to about 0.1 weight percent in product.

The present invention also provides methods of treating and/or reducing inflammation and/or redness on the skin caused by any of a variety of sources, including, but not limited to, various forms of eczema and psoriasis, acne and rosacea, contact irritant and allergic dermatitis, sunlight-induced dermatoses, infections caused by foreign organisms, insect bites, physical abrasion, and dry skin. In certain embodiments, such methods comprise contacting skin in need of anti-inflammatory treatment with a composition of the present invention described above. In certain preferred embodiments, the present methods comprise contacting the skin with a composition comprising an anti-inflammatory agent selected from the group consisting of olive leaf extract, holly herb, sappan wood, feverfew, and combinations of two or more thereof and an agent comprising at least one lipoaminoacid and at least one metal salt. In certain other embodiments, the present invention provides methods of treating and/or reducing inflammation on the skin by contacting skin in need of anti-inflammatory treatment with a personal care product comprising a composition of the present invention.

The compositions and/or personal care products of the present invention may be contacted with skin via any of a variety of means according to the present methods. For example, the compositions and products may be applied topically to the skin, hair, or nails. Preferably, in certain embodiments, the compositions and/or products are applied topically to the skin.

Applicants have recognized that the present methods allow for the reduction of redness, and more generally, the reduction of inflammation to the skin in a manner more effective than comparable methods.

EXAMPLES

The invention is further illustrated in the following examples that are intended to be illustrative, but not limiting in any manner.

Example 1

Evaluation on RAW 264 Macrophage Cell Line

Mononuclear phagocytes, or macrophages, are found in large numbers of the skin and are an important component of the innate immune response. In skin, macrophages are the primary cells involved in recognizing and eliminating foreign pathogens such as bacteria through production of nitric oxide, a potent pro-inflammatory mediator. However, release of nitric oxide can also result in skin inflammation and damage to adjacent skin cells and unregulated nitric oxide production can result in tissue injury. The ability of Olive Leaf Extract, Sepicalm or a combination of Olive Leaf Extract and Sepicalm to affect the inflammatory response was illustrated by its ability to reduce macrophage activation in the following assay.

The murine macrophage cell line (RAW264) cells were adjusted to a density of $4 \times 10^{5^6}$ cells/mL in DMEM with 10% FBS (American Type Culture Collection, Manassas, Va.) and 100 µL was added to a flat-bottomed 96-well tissue culture plate. Murine macrophage cells were stimulated with 1 µg/ml of the bacterial cell well component, lipopolysaccharide (LPS) as positive control or in the presence or absence of Olive Leaf Extract, Sepicalm or a combination of Olive Leaf Extract and Sepicalm. Macrophages cultures were treated for 24 hours at 37° C. with 5% $CO_2$ in the presence or absence of test samples then Nitrites formation, the stable end product of nitric oxide, were assayed with the Griess assay. Results are expressed as the percent inhibition of inflammatory mediator production compared to a stimulated control culture.

| RAW 264 Murine Macrophages Stimulated by LPS | | |
|---|---|---|
| Test material (Concentration) | Percent (%) Inhibition of Nitric Oxide Release | Ratio Sepicalm: Olive Leaf Extract |
| Olive Leaf extract (.01%) | 6.5 +/− 0.8 | 1:1 |
| Sepicalm (.01%) | 12.1 +/− 0.05 | |
| Olive Leaf Extract (.01%) + Sepicalm (.01%) | 20.9 +/− 0.02* | |

| RAW 264 Murine Macrophages Stimulated by LPS | | |
|---|---|---|
| Test material (Concentration) | Percent (%) Inhibition of Nitric Oxide Release | Ratio Sepicalm: Olive Leaf Extract |
| Olive Leaf extract (.02%) | 24.5 +/− 1.2 | 1:1 |
| Sepicalm (.02%) | 27.1 +/− 1.1 | |
| Olive Leaf Extract (.02%) + Sepicalm (.02%) | 77.2 +/− 0.1* | |
| Olive Leaf (.005%) | 1.31 +/− 0.6 | 4:1 |
| Sepicalm (.02%) | 32.1 +/− 0.6 | |
| Olive Leaf (.005%) + Sepicalm (.02%) | 39.8 +/− 1.4* | |
| Sepicalm (.005%) | 3.26 +/− 1.5 | 1:4 |
| Olive Leaf (.02%) | 16.6 +/− 0.6 | |
| Sepicalm (.005%) + Olive Leaf (.02%) | 29.31 +/− 2.1* | |

*= $P < 0.05$ compared to Olive Leaf Extract or Sepicalm alone using an unpaired students t-Test While both Olive Leaf Extract and Sepicalm have moderate anti-inflammatory activity individually, we surprisingly found that a combination of Olive Leaf Extract and Sepicalm is remarkably effective in reducing inflammation. The anti-inflammatory activity of the combination of Olive Leaf Extract and Sepicalm is greater than the sum of the individual activities, indicating that the combination of Olive Leaf Extract and Sepicalm has a synergistic response.

Example 2

Comparison of Sepicalm Potentiation of Water Soluble Vs Oil Soluble Natural Extracts in RAW 264 Macrophage Cell Line The ability of Sepicalm to synergistically enhance the anti-inflammatory activity of water soluble and oil soluble extracts of natural materials was illustrated by its ability to reduce macrophage activation in the following assay.

The murine macrophage cell line (RAW264) cells were adjusted to a density of $4 \times 10^{5^6}$ cells/mL in DMEM with 10% FBS (American Type Culture Collection, Manassas, Va.) and 100 µL was added to a flat-bottomed 96-well tissue culture plate. Murine macrophage cells were stimulated with 0.1 µg/ml of the bacterial cell well component, lipopolysaccharide (LPS) as positive control or in the presence or absence of Sepicalm, water soluble extracts (*Siegesbeckia* and *Lignum Sappan*), partially water soluble/partially oil soluble extracts (Feverfew), oil soluble extracts (Oat Oil Extract, *Boswellia Serrata* Oil Extract) or a combination of extract plus Sepicalm. Sigesbeckia, so called the Holy Herb, is an aqueous extract. (Sederma Edison N.J.). In China it is used as a remedy for ague, rheumatism, and renal colic; used in Britain chiefly as a cure for ringworm in conjunction with glycerine. *Lignum Sappan* also called Sappan Wood, is an aqueous extract of dried heart wood of *Caesalpinia sappan*. It is used to promote blood circulation and remove blood stasis, and to cause subsidence of swelling and relieve pain. Feverfew has both water soluble and oil soluble components. (Indena, Milan Italy). *Tanacetum parthenium*, a plant commonly known as Feverfew, has been recognized since the Middle Ages as having significant medicinal properties when taken orally—used as a general febrifuge, hence its common name. *Boswellia Serrata* oil extract (Quest Intl, South Plainfield, N.J.) also called Frankincense is an extract of the oleo-gum resin of the tree, *Boswellia serrata*, found in the dry forests in parts of India. Its oleo-gum resin is fragrant, transparent and brownish yellow in color. The main ingredients of the extract are three triperpene acids, ☐, ☐, and ☐-boswellic acids, of which □-boswellic acid has been shown to be responsible for the anti-tumor and anti-arthritic properties of *Boswellia serrata*. Oat oil extract (Dragoco, Totowa, N.J.) isolated from oat, *Avena sativa*, has been used as an anti-irritant and an antioxidant. Macrophage cultures were treated for 24 hours at 37° C. with 5% $CO_2$ in the presence or absence of test samples then Nitrites formation, the stable end product of nitric oxide, were assayed for with the Griess assay. Results are expressed as the percent inhibition of inflammatory mediator production compared to a stimulated control culture.

RAW 264 Murine Macrophages Stimulated by LPS

| Test material (concentration) | Percent (%) Inhibition of Nitric Oxide Release | Physical Solubility |
|---|---|---|
| Sepicalm (200 ug/ml) | 10.58 +/− 0.7 | |
| Siegesbeckia (2 ug/ml) | 20.2 +/− 1.7 | Water Soluble |
| Siegesbeckia (2 ug/ml) + Sepicalm (200 ug/ml) | 53.9 +/− 0.8* | |
| Lignum Sapen (20 ug/ml) | 25.9 +/− 5.2 | Water Soluble |
| Lignum Sapen (20 ug/ml) + Sepicalm (200 ug/ml) | 66.8 +/− 1.3* | |
| Feverfew (80 ug/ml) | 36.0 +/− 1.0 | Water Soluble/Oil Soluble |
| Feverfew (80 ug/ml) + Sepicalm (200 ug/ml) | 55.63 +/− 1.9* | |
| Oat Oil Extract (50 ug/ml) | 8.3 +/− 3.6 | Oil Soluble |
| Oat Oil Extract (50 ug/ml) + Sepicalm (200 ug/ml) | 12.5 +/− 0.6 | |
| Boswellia Serrata Oil Extract (50 ug/ml) | 8.7 +/− 3.1 | Oil Soluble |
| Boswellia Serrata Oil Extract (50 ug/ml) + Sepicalm (200 ug/ml) | 17.55 +/− 0.6 | |

*= $P < 0.05$ compared to compound/extract alone using a paired students t-Test

Sepicalm was shown to produce a synergistic increase in anti-inflammatory activity of water soluble extracts (*Siegesbeckia* and *Lignum Sapen*), and partially water soluble/partially oil soluble extracts (Feverfew), but didn't synergistically increase anti-inflammatory activity of oil soluble extracts (Oat Oil Extract, *Boswellia Serrata* Oil Extract). These findings demonstrate that Sepicalm can potentiate the activity of water soluble extracts and partially water soluble/partially oil soluble extracts.

Example 3

A study was performed on four adult Caucasian females having the skin type 1-3 on the Fitzpatrick scale. No lotion/product use was allowed during the study in the areas designated for the study.

The skin of volunteer subjects was induced to dry out during a conditioning period. Subjects were asked to follow a skin-dry out protocol for 7 days prior to the study. This consisted of washing both legs (from the knee below) with Ivory soap twice a day. This protocol was continued during the course of the study.

For the study, assessments were made both before and 4 hours after a fixed amount of product was applied. Irritation was also induced onto a separate site on the leg using a shaving protocol prior to product application on days 1 and 3 only, and measures taken as described above. Two products were tested; a product containing an active composition consisting of 1.0% Sepicalm, 0.01% Olive Leaf, and 0.5% Coviox T90 (the "active" product) and an identically formulated placebo product ("placebo"), having only 0.01% olive leaf as the anti-inflammatory active.

Assessments included the evaluation of skin redness, quantified using Diffuse reflectance spectroscopy (DRS) to measure absorption by oxyhemoglobin.

Percent change in skin redness 4 hours after each treatment on dry skin.

| | Day 1 | Day 2 | Day 3 | Day 4 |
|---|---|---|---|---|
| Active | 24.65% | −37.81% | −22.52% | −27.13% |
| SE | 17.53% | 8.35% | 10.04% | 9.48% |
| Placebo | 31.74% | −12.68% | 4.86% | 6.31% |
| SE | 27.12% | 12.28% | 23.59% | 22.19% |

Percent change in skin redness 4 hours after each treatment on dry, irritated skin.

| | Day 1 | Day 2 | Day 3 | Day 4 |
|---|---|---|---|---|
| Active | 7.67% | −39.69% | −31.78% | −1.13% |
| SE | 7.19% | 11.59% | 9.79% | 13.37% |
| Placebo | 15.88% | −3.86% | −1.96% | −5.80% |
| SE | 23.97% | 26.25% | 11.39% | 11.43% |

Example 4

The blend of ingredients that have demonstrated a beneficial synergist effect may be incorporated into various types of products. The products may include but are not limited to—emulsion, surfactant, anhydrous, tablet/powder, & polymeric systems. Examples of each system type ingredient ranges and the upper and lower limits of the synergistic components are identified as well.

4A - Emulsion Systems - Leave On

| Components | % w/w Range of Composition | |
|---|---|---|
| | Lower | Upper |
| Water Phase—water/viscosifying ing/surfactant, all other water soluble ingredients | 30.0000 | 98.0000 |
| Oil Phase/Emollients, Waxes, Fatty Alcohols, Surfactants, all other oil soluble/miscible ingredients. | 2.0000 | 70.0000 |
| Solids for skin look, feel, protection | 0.0010 | 15.0000 |
| Olive Leaf Extract | 0.0001 | 0.7500 |
| Sodium Cocoyl aminoacids, Sarcosine, Potassium Aspartate, Magnesium Aspartate, propylene glycol, water | 0.0050 | 10.0000 |
| Additional naturally derived/sourced ingredients with known beneficial properties for additive effect | 0.0050 | 10.0000 |

4B - Surfactant Systems (Rinse Off)

| Components | % w/w Range of Composition | |
|---|---|---|
| | Lower | Upper |
| Water Phase—water/viscosifying ing, surfactant. | 2.0000 | 98.0000 |
| Oil Phase/Emollients, Waxes, Fatty Alcohols, Surfactants | 2.0000 | 98.0000 |
| Solids for skin look, feel, protection | 0.0010 | 15.0000 |
| Olive Leaf Extract | 0.0001 | 0.7500 |

-continued

4B - Surfactant Systems (Rinse Off)

| Components | % w/w Range of Composition | |
|---|---|---|
| | Lower | Upper |
| Sodium Cocoyl aminoacids, Sarcosine, Potassium Aspartate, Magnesium Aspartate, propylene glycol, water | 0.0050 | 10.0000 |
| Additional naturally derived/sourced ingredients with known beneficial properties for additive effect | 0.0050 | 10.0000 |

4C - Surfactant Systems (solid)

| Components | % w/w Range of Composition | |
|---|---|---|
| | Lower | Upper |
| Soap Base | 1.0000 | 99.0000 |
| Surfactant Base (non-soap) | 1.0000 | 99.0000 |
| Emollients/Skin Conditioners | 0.0500 | 10.0000 |
| Fragrance | 0.0000 | 2.0000 |
| Disodium EDTA | 0.0100 | 1.0000 |
| Purified Water | 0.0000 | 10.0000 |
| Olive Leaf Extract | 0.0001 | 0.7500 |
| Sodium Cocoyl aminoacids, Sarcosine, Potassium Aspartate, Magnesium Aspartate, propylene glycol, water | 0.0050 | 10.0000 |
| Additional naturally derived/sourced ingredients with known beneficial properties for additive effect | 0.0050 | 10.0000 |

4D - Polymer Systems - Leave On or Rinse Off

| Components | % w/w Range of Composition | |
|---|---|---|
| | Lower | Upper |
| Water Phase—water/viscosifying ing/ | 15.0000 | 98.0000 |
| Oil Phase/Emollients, Waxes, Fatty Alcohols, | 2.0000 | 85.0000 |
| Polymer Systems | 1.0000 | 10.0000 |
| Solids for skin look, feel, protection | 0.0010 | 15.0000 |
| Olive Leaf Extract | 0.0001 | 0.7500 |
| Sodium Cocoyl aminoacids, Sarcosine, Potassium Aspartate, Magnesium Aspartate, propylene glycol, water | 0.0050 | 10.0000 |
| Additional naturally derived/sourced ingredients with known beneficial properties for additive effect | 0.0050 | 10.0000 |

4E - Powder or Tablets - Leave On or Dissolvable

| Components | % w/w Range of Composition | |
|---|---|---|
| | Lower | Upper |
| Corn Starch | 0.5000 | 99.0000 |
| Talc | 0.5000 | 99.0000 |
| Dilutent/Filler/Vechicle | 0.0000 | 25.0000 |
| Binder/Caking Agent | 0.0000 | 40.0000 |
| Lubricant | 0.0000 | 10.0000 |
| Disintegrant | 0.0000 | 25.0000 |
| Solids for skin look, feel, protection | 0.0010 | 15.0000 |
| Olive Leaf Extract | 0.0001 | 0.7500 |
| Sodium Cocoyl aminoacids, Sarcosine, Potassium Aspartate, Magnesium Aspartate, propylene glycol, water | 0.0050 | 10.0000 |
| Additional naturally derived/sourced ingredients with known beneficial properties for additive effect | 0.0050 | 10.0000 |

4F - Anhydrous Product

| Components | % w/w Range of Composition | |
|---|---|---|
| | Lower | Upper |
| Liquid @ 25C, non-freely water soluble ingredients ie) esters, mineral oil, soybean oil etc | 0.01 | 99.9900 |
| Solid 0-37C non-freely water soluble ingredients | 0 | 99.0000 |
| Self Emulsifying Waxes | 0 | 15.0000 |
| Humectant | 0.05 | 3.0000 |
| Flavor/Fragrance | 0.3 | 10.0000 |
| Olive Leaf Extract | 0.0001 | 0.7500 |
| Sodium Cocoyl aminoacids, Sarcosine, Potassium Aspartate, Magnesium Aspartate, propylene glycol, water | 0.0050 | 10.0000 |
| Additional naturally derived/sourced ingredients with known beneficial properties for additive effect | 0.0050 | 10.0000 |

Products described in Examples 4A-4F are made via the following procedure(s):

Manufacturing instructions for systems containing oil & water:

1) Combine water phase ingredients, mix and heat until homogeneous
2) Combine oil phase ingredients, mix and heat until homogeneous
3) When both phases are at equal temperature, add the oil phase to the water phase with mixing.
4) Mix until uniform, homogenize if necessary.
5) Add preservatives and fragrances after cooling.

Manufacturing instructions for anhydrous systems:
1) Place all ingredients into primary kettle
2) Heat with mixing until phase is uniform
3) Pour into molds or packaging and allow to cool.

What is claimed is:

1. A method of reducing skin irritation or redness in a subject with skin in need of inflammation reduction comprising contacting the skin in need of inflammation reduction with a personal care product, said personal care product comprising a therapeutically effective amount of a composition with anti-inflammatory properties comprising (a) an anti-inflammatory agent comprising olive leaf (*Olea Europea*) extract in an amount of from 0.0001 to about 0.75 weight percent of said personal care product, and (b) an anti-inflammatory agent comprising a combination of sodium cocoyl amino acids, magnesium aspartate, and potassium aspartate in combination with sarcosine in a cosmetically acceptable vehicle, in an amount of from 0.005 to about 10 percent by weight of said personal care product, wherein said anti-inflammatory ingredient (a) and said anti-inflammatory ingredient (b) are present in the anti-inflammatory composition in a ratio of 4:1 and said anti-inflammatory composition is present in the personal care product in an amount of from greater than zero to about 5 weight percent.

2. The method of claim 1, wherein said personal care product comprises said a composition with anti-inflammatory properties in an amount of from about 0.02 to about 4 weight percent in said personal care product.

3. The method of claim 1, wherein said personal care product comprises said a composition with anti-inflammatory properties in an amount of from about 0.02 to about 0.1 weight percent in said personal care product.

4. The method of claim 1, wherein said irritation is caused by dry skin or physical abrasion.

5. A method of reducing skin irritation or redness in a subject with skin in need of inflammation reduction comprising contacting the skin in need of inflammation reduction with a personal care product, said personal care product comprising a therapeutically effective amount of a composition with anti-inflammatory properties comprising (a) an anti-inflammatory agent comprising olive leaf (*Olea Europea*) extract in an amount of about 0.02 weight percent of said personal care product, and (b) an anti-inflammatory agent comprising a combination of sodium cocoyl amino acids, magnesium aspartate, and potassium aspartate in combination with sarcosine in a cosmetically acceptable vehicle, in an amount of about 0.005 percent by weight in said personal care product.

\* \* \* \* \*